United States Patent
Moorehead et al.

(10) Patent No.: US 12,286,415 B2
(45) Date of Patent: Apr. 29, 2025

(54) CANNABIS PROCESSING SYSTEMS AND METHODS

(71) Applicant: Soma Oil LLC, Salt Lake City, UT (US)

(72) Inventors: John Moorehead, Huntsville, UT (US); Emily Drown, Salt Lake City, UT (US); Ken Rivera, St. George, UT (US); Terry A. Ring, Sandy, UT (US); Ahron Barber, Salt Lake City, UT (US)

(73) Assignee: Soma Oil LLC, Salt Lake City, UT (US)

( * ) Notice: Subject to any disclaimer, the term of this patent is extended or adjusted under 35 U.S.C. 154(b) by 95 days.

(21) Appl. No.: 17/808,877

(22) Filed: Jun. 24, 2022

(65) Prior Publication Data

US 2022/0324828 A1    Oct. 13, 2022

Related U.S. Application Data

(63) Continuation of application No. 16/856,713, filed on Apr. 23, 2020, now Pat. No. 11,370,767.

(60) Provisional application No. 62/837,613, filed on Apr. 23, 2019.

(51) Int. Cl.
| | | |
|---|---|---|
| *C07D 311/78* | (2006.01) | |
| *B01D 3/10* | (2006.01) | |
| *B01D 11/02* | (2006.01) | |

(52) U.S. Cl.
CPC .............. *C07D 311/78* (2013.01); *B01D 3/10* (2013.01); *B01D 11/0288* (2013.01)

(58) Field of Classification Search
CPC ...... C07D 311/78; B01D 3/10; B01D 11/0288
See application file for complete search history.

(56) References Cited

U.S. PATENT DOCUMENTS

| | | |
|---|---|---|
| 3,710,805 A | 1/1973 | Tamaki et al. |
| 6,365,416 B1 | 4/2002 | Elsohly et al. |
| 6,403,126 B1 | 6/2002 | Webster et al. |
| 7,344,736 B2 | 3/2008 | Whittle et al. |
| 7,524,881 B2 | 4/2009 | Goodwin et al. |
| 8,343,553 B2 | 1/2013 | Hospodor |
| 8,530,679 B2 | 9/2013 | Bhatarah et al. |
| 8,846,409 B2 | 9/2014 | Flockhart et al. |
| 9,155,767 B2 | 10/2015 | Hospodor et al. |
| 9,358,259 B2 | 6/2016 | Hospodor et al. |
| 9,730,911 B2 | 8/2017 | Verzura et al. |
| 9,987,567 B1 | 6/2018 | Ko |
| 10,011,804 B2 | 7/2018 | Mancosky |
| 10,059,684 B2 | 8/2018 | Changoer et al. |
| 10,092,611 B1 | 10/2018 | Speier |
| 10,143,706 B2 | 12/2018 | Kotra et al. |
| 2003/0017216 A1 | 1/2003 | Schmidt et al. |
| 2003/0050334 A1 | 3/2003 | Murty et al. |
| 2006/0167283 A1 | 7/2006 | Flockhart et al. |
| 2007/0093665 A1 | 4/2007 | Burdick et al. |
| 2008/0167483 A1 | 7/2008 | Whittle et al. |
| 2014/0248379 A1 | 9/2014 | Mueller |
| 2014/0271940 A1 | 9/2014 | Wurzer |
| 2015/0152018 A1 | 6/2015 | Raber et al. |
| 2016/0346339 A1 | 12/2016 | Finley et al. |
| 2017/0008870 A1 | 1/2017 | Dibble et al. |
| 2017/0051231 A1 | 2/2017 | Mancosky |
| 2017/0252384 A1 | 9/2017 | Goldner |
| 2017/0333809 A1 | 11/2017 | Lopa |
| 2018/0282250 A1 | 10/2018 | Rutz et al. |
| 2019/0241536 A1 | 8/2019 | Durkacz et al. |

FOREIGN PATENT DOCUMENTS

| | | |
|---|---|---|
| CA | 3005014 A1 | 11/2018 |
| EP | 3461546 A1 | 4/2019 |
| WO | 99/38392 A1 | 8/1999 |
| WO | 2018/195562 A1 | 10/2018 |
| WO | 2018/020738 A1 | 1/2019 |

OTHER PUBLICATIONS

International Search Report for Application No. PCT/US2020/029542, mailed Aug. 12, 2020, 2 pages.
Nair G.R. et al., "Electro-osmotic Dewatering of Soaked Hemp Stems, Drying Technology", Drying Technology, 2017, vol. 35, issue 8, pp. 999-1006; retrieved from the Internet: <DOI:10.1080/07373937.2016.1225219>, see entire document, especially, pp. 999, 1004.
Written Opinion of the International Searching Authority for Application No. PCT/US2020/029542, mailed Aug. 12, 2020, 6 pages.
Ahmed et al., Cannabinoid Ester Constituents from High-Potency Cannabis Sativa, Journal of Natural Products, vol. 71, No. 4, (Apr. 1, 2008) 7 pages.
Australian Patent Examination Report No. 1 for Australian Application No. 2020262269, dated Apr. 4, 2023, 3 pages.
Canadian Requisition by the Examiner for Canadian Application No. 3137735, dated Jan. 26, 2023, 4 pages.

(Continued)

*Primary Examiner* — Sikarl A Witherspoon
(74) *Attorney, Agent, or Firm* — TraskBritt

(57) ABSTRACT

A *Cannabis* processing system comprises a grinding apparatus and a cell disruption apparatus. The grinding apparatus is configured to grind wet *Cannabis* cuttings to from a ground, wet *Cannabis* material comprising wet *Cannabis* particles having an average particle size within a range of from about 1 mm to about 3 mm. The cell disruption apparatus is downstream of the grinding apparatus and is configured to disrupt cell walls of plant cells of the wet *Cannabis* particles through one or more of flash freezing, a cellulose solvent, applied negative pressure, and vacuum distillation to facilitate removal of one or more cannabinoids within the plant cells of the wet *Cannabis* particles. Methods of processing *Cannabis* are also described.

16 Claims, 12 Drawing Sheets

(56) References Cited

OTHER PUBLICATIONS

European Extended Search Report and Opinion for European Application No. 20796148.3, dated Nov. 23, 2022, 10 pages.
Nayland Stanley-Wood, Particle Size Analysis: Introduction, Encyclopedia of Analytical Chemistry, Meyers R A (Ed.), John Wiley & Sons Ltd, (Jan. 1, 2005) 37 pages.
Tekin et al., Ethanol: A Promising Green Solvent for the Deconstruction of Lignocellulose, ChemSusChem, vol. 11, No. 20, (Oct. 24, 2018) 17 pages.

| - MIXED Substream | Units | S9 ▸ | S14 ▸ | S12 ▸ | S13 ▸ | S15 ▸ | S16 ▸ | S18 ▸ | S19 ▸ |
|---|---|---|---|---|---|---|---|---|---|
| Phase | | Liquid Phase | Liquid Phase | Liquid Phase | Liquid Phase | Liquid Phase | Liquid Phase | Liquid Phase | Liquid Phase |
| Temperature | C | -50 | -25.1422 | 74.9767 | 82.5459 | 5 | 5 | 30 | -70 |
| Pressure | bar | 1.2 | 1.1 | 1 | 1.19995 | 1 | 1 | 1.1 | 1 |
| Molar Vapor Fraction | | 0 | 0 | 0 | 0 | 0 | 0 | 0 | 0 |
| Molar Liquid Fraction | | 1 | 1 | 1 | 1 | 1 | 1 | 1 | 1 |
| Molar Solid Fraction | | 0 | 0 | 0 | 0 | 0 | 0 | 0 | 0 |
| Mass Vapor Fraction | | 0 | 0 | 0 | 0 | 0 | 0 | 0 | 0 |
| Mass Liquid Fraction | | 1 | 1 | 1 | 1 | 1 | 1 | 1 | 1 |
| Mass Solid Fraction | | 0 | 0 | 0 | 0 | 0 | 0 | 0 | 0 |
| Molar Enthalpy | cal/mol | -69837.2 | -69144.5 | -64770.3 | -67437.2 | -69115.6 | -102457 | -68880.5 | -69403.7 |
| Mass Enthalpy | cal/gm | -1617.43 | -1601.38 | -1475.03 | -1591.12 | -3836.5 | -339.466 | -1625.18 | -1580.54 |
| Molar Entropy | cal/mol-K | -79.0492 | -76.1056 | -74.1151 | -58.7552 | -41.4731 | -377.12 | -63.1423 | -91.2194 |
| Mass Entropy | cal/gm-K | -1.83078 | -1.7626 | -1.68784 | -1.38628 | -2.30211 | -1.2495 | -1.48979 | -2.07735 |
| Molar Density | mol/cc | 0.021932 | 0.021435 | 0.016928 | 0.0218455 | 0.0562327 | 0.00467578 | 0.0227289 | 0.0206306 |
| Mass Density | gm/cc | 0.94698 | 0.925518 | 0.743333 | 0.925886 | 1.01305 | 1.41123 | 0.963328 | 0.905917 |
| Enthalpy Flow | cal/sec | -19399.2 | -19206.8 | -9355.71 | -899.163 | -8424.15 | -1172.97 | -9184.06 | -10025 |
| Average MW | | 43.1779 | 43.1779 | 43.9113 | 42.3834 | 18.0153 | 301.816 | 42.3834 | 43.9113 |
| + Mole Flows | kmol/hr | 1 | 1 | 0.52 | 0.48 | 0.438786 | 0.0412144 | 0.48 | 0.52 |
| + Mole Fractions | | | | | | | | | |

FIG. 7A

| | | | | | | | | | |
|---|---|---|---|---|---|---|---|---|---|
| - Mass Flows | kg/hr | 43.1779 | 43.1779 | 22.8339 | 20.344 | 7.90485 | 12.4392 | 20.344 | 22.8339 |
| CB | kg/hr | 12.4174 | 12.4174 | 0.000155857 | 12.4173 | 1.47973e-34 | 12.4173 | 12.4173 | 0.000155857 |
| ETHANOL | kg/hr | 22.1131 | 22.1131 | 22.1131 | 1.47682e-14 | 0 | 0 | 1.47682e-14 | 22.1131 |
| ISOPR-01 | kg/hr | 0 | 0 | 0 | 0 | 0 | 0 | 0 | 0 |
| WATER | kg/hr | 8.64733 | 8.64733 | 0.720602 | 7.92673 | 7.90485 | 0.0218867 | 7.92673 | 0.720602 |
| - Mass Fractions | | | | | | | | | |
| CB | | 0.287588 | 0.287588 | 6.82569e-06 | 0.610366 | 1.87193e-35 | 0.998241 | 0.610366 | 6.82569e-06 |
| ETHANOL | | 0.51214 | 0.51214 | 0.968435 | 7.25923e-16 | 0 | 0 | 7.25923e-16 | 0.968435 |
| ISOPR-01 | | 0 | 0 | 0 | 0 | 0 | 0 | 0 | 0 |
| WATER | | 0.200272 | 0.200272 | 0.0315584 | 0.389634 | 1 | 0.0017595 | 0.389634 | 0.0315584 |
| Volume Flow | l/min | 0.759923 | 0.777545 | 0.511971 | 0.366208 | 0.130051 | 0.146907 | 0.351975 | 0.420088 |
| Mass heat capacity, mixture | cal/gm-K | 0.641035 | 0.651015 | 0.799309 | 0.665386 | 1.08364 | 0.390204 | 0.631845 | 0.692045 |

FIG. 7B

| | Units | S9 | S11 | S12 | S13 | S14 | S15 | S16 | S18 | S19 |
|---|---|---|---|---|---|---|---|---|---|---|
| Phase | | Liquid Phase | | Liquid Phase | Liquid Phase | Liquid Phase | Liquid Phase | | Liquid Phase | Liquid Phase |
| Temperature | C | -50 | | 80.7604 | 125.836 | 8.8154 | 5 | | 30 | -50 |
| Pressure | bar | 1.2 | 1 | 1 | 1.19995 | 1.1 | 1 | 1 | 1.1 | 1 |
| Molar vapor Fraction | | 0 | | 0 | 0 | 0 | 0 | | 0 | 0 |
| Molar Liquid Fraction | | 1 | | 1 | 1 | 1 | 1 | | 1 | 1 |
| Molar Solid Fraction | | 0 | | 0 | 0 | 0 | 0 | | 0 | 0 |
| Mass Vapor Fraction | | 0 | | 0 | 0 | 0 | 0 | | 0 | 0 |
| Mass Liquid Fraction | | 1 | | 1 | 1 | 1 | 1 | | 1 | 1 |
| Mass Solid Fraction | | 0 | | 0 | 0 | 0 | 0 | | 0 | 0 |
| Molar Enthalpy | cal/mol | -75062 | | -68103.8 | -74104.4 | -73176.9 | -80754.9 | | -79490.4 | -71394.9 |
| Mass Enthalpy | cal/gm | -1325.16 | | -2083.35 | -732.763 | -1291.88 | -798.526 | | -786.021 | -2184.03 |
| Molar Entropy | cal/mol-K | -101.914 | | -55.8811 | -140.72 | -94.4253 | -160.451 | | -156.1 | -67.4421 |
| Mass Entropy | cal/gm-K | -1.7992 | | -1.70945 | -1.39148 | -1.667 | -1.58658 | | -1.54356 | -2.06311 |
| Molar Density | mol/cc | 0.0166432 | | 0.0254263 | 0.0077925 | 0.0157718 | 0.00868889 | | 0.00850634 | 0.0297042 |
| Mass Density | gm/cc | 0.942735 | | 0.831173 | 0.784693 | 0.893371 | 0.878708 | | 0.860247 | 0.971018 |
| Enthalpy Flow | cal/sec | -20850.5 | | -12296.5 | -7204.59 | -20326.9 | -7851.18 | | -7728.23 | -12890.7 |
| Average MW | | 56.6437 | | 32.6896 | 101.13 | 56.6437 | 101.13 | | 101.13 | 32.6896 |
| + Mole Flows | kmol/hr | 1 | 0 | 0.65 | 0.35 | 1 | 0.35 | 0 | 0.35 | 0.65 |
| + Mole Fractions | | | | | | | | | | |

FIG. 8A

| Mass Flows | kg/hr | 56.6437 | 21.2482 | 35.3955 | 56.6437 | 35.3955 | 35.3955 | 21.2482 |
|---|---|---|---|---|---|---|---|---|
| CB | kg/hr | 12.4174 | 4.32828e-133 | 12.4174 | 12.4174 | 12.4174 | 12.4174 | 4.32828e-133 |
| ETHANOL | kg/hr | 0 | 0 | 0 | 0 | 0 | 0 | 0 |
| ISOPR-01 | kg/hr | 0 | 0 | 0 | 0 | 0 | 0 | 0 |
| WATER | kg/hr | 8.64733 | 8.64733 | 3.63742e-13 | 8.64733 | 3.63742e-13 | 3.63742e-13 | 8.64733 |
| BUTANOL | kg/hr | 35.5789 | 12.6009 | 22.9781 | 35.5789 | 22.9781 | 22.9781 | 12.6009 |
| PROPANOL | kg/hr | 0 | 0 | 0 | 0 | 0 | 0 | 0 |
| Mass Fractions | | | | | | | | |
| CB | | 0.21922 | 2.03701e-134 | 0.35082 | 0.21922 | 0.35082 | 0.35082 | 2.03701e-134 |
| ETHANOL | | 0 | 0 | 0 | 0 | 0 | 0 | 0 |
| ISOPR-01 | | 0 | 0 | 0 | 0 | 0 | 0 | 0 |
| WATER | | 0.152662 | 0.406968 | 1.02765e-14 | 0.152662 | 1.02765e-14 | 1.02765e-14 | 0.406968 |
| BUTANOL | | 0.628118 | 0.593032 | 0.64918 | 0.628118 | 0.64918 | 0.64918 | 0.593032 |

FIG. 8B

| | Units | S9 | S11 | S12 | S13 | S14 | S15 | S16 | S18 | S19 |
|---|---|---|---|---|---|---|---|---|---|---|
| Phase | | Liquid Phase | | Liquid Phase | Liquid Phase | Liquid Phase | Liquid Phase | | Liquid Phase | Liquid Phase |
| Temperature | C | -50 | | 83.2032 | 106.616 | -32.2668 | 5 | | 30 | -50 |
| Pressure | bar | 1.2 | 1 | 1 | 1.19995 | 1.1 | 1 | 1 | 1.1 | 1 |
| Molar Vapor Fraction | | 0 | | 0 | 0 | 0 | 0 | | 0 | 0 |
| Molar Liquid Fraction | | 1 | | 1 | 1 | 1 | 1 | 1 | 1 | 1 |
| Molar Solid Fraction | | 0 | | 0 | 0 | 0 | 0 | | 0 | 0 |
| Mass Vapor Fraction | | 0 | | 0 | 0 | 0 | 0 | | 0 | 0 |
| Mass Liquid Fraction | | 1 | | 1 | 1 | 1 | 1 | | 1 | 1 |
| Mass Solid Fraction | | 0 | | 0 | 0 | 0 | 0 | | 0 | 0 |
| Molar Enthalpy | cal/mol | -72440.9 | | -69864.8 | -67127.7 | -71915.6 | -69115.6 | | -68628.5 | -74975.5 |
| Mass Enthalpy | cal/gm | -1451.41 | | -1041.43 | -3726.16 | -1440.88 | -3836.5 | | -3809.46 | -4117.61 |
| Molar Entropy | cal/mol-k | -90.1996 | | -99.5175 | -35.3843 | -87.9341 | -41.4731 | | -39.7962 | -117.344 |
| Mass Entropy | cal/gm-k | -1.80722 | | -1.48345 | -1.9613 | -1.76182 | -2.30221 | | -2.20902 | -1.74918 |
| Molar Density | mol/cc | 0.0188889 | | 0.0120431 | 0.050582 | 0.0185899 | 0.0562327 | | 0.549045 | 0.0137157 |
| Mass Density | gm/cc | 0.942761 | | 0.807917 | 0.911249 | 0.927839 | 1.01305 | | 0.989121 | 0.920125 |
| Enthalpy Flow | cal/sec | -201.1225 | | -12614.5 | -6526.31 | -19976.6 | -6719.56 | | -6672.21 | -13537.2 |
| Average MW | | 49.9106 | | 67.0854 | 18.0153 | 49.9108 | 18.0153 | | 18.0153 | 67.0853 |
| + Mole Flows | kmol/hr | 1 | 0 | 0.65 | 0.35 | 1 | 0.35 | 0 | 0.35 | 0.65 |
| + Mole Fractions | | | | | | | | | | |

FIG. 9A

| Mass Flows | kg/hr | 49.9108 | 43.6055 | 6.30535 | 49.9108 | 6.30535 | 43.6055 |
|---|---|---|---|---|---|---|---|
| CB | kg/hr | 12.4174 | 12.4174 | 5.508e-144 | 12.4174 | 0 | 12.4174 |
| ETHANOL | kg/hr | 0 | 0 | 0 | 0 | 0 | 0 |
| ISOPR-01 | kg/hr | 0 | 0 | 0 | 0 | 0 | 0 |
| WATER | kg/hr | 8.64733 | 2.34199 | 6.30535 | 8.64733 | 6.30535 | 2.34199 |
| BUTANOL | kg/hr | 0 | 0 | 0 | 0 | 0 | 0 |
| PROPANOL | kg/hr | 28.846 | 28.846 | 1.60781e-44 | 28.646 | 0 | 28.846 |
| Mass Fractions | | | | | | | |
| CB | | 0.248793 | 0.284768 | 8.73544e-145 | 0.248793 | 0 | 0.284768 |
| ETHANOL | | 0 | 0 | 0 | 0 | 0 | 0 |
| ISOPR-01 | | 0.173256 | 0.0537085 | 1 | 0.173256 | 1 | 0.0537085 |
| WATER | | 0 | 0 | 0 | 0 | 0 | 0 |
| BUTANOL | | 0.577952 | 0.661523 | 2.5499e-45 | 0.577952 | 0 | 0.661523 |
| PROPANOL | | 0.882352 | 0.899546 | 0.115324 | 0.896543 | 0.103736 | 0.789847 |
| Volume Flow | l/min | | | | | | 0.106245 |

FIG. 9B

CANNABIS PROCESSING SYSTEMS AND METHODS

CROSS-REFERENCE TO RELATED APPLICATIONS

This application is a continuation of U.S. patent application Ser. No. 16/856,713, filed Apr. 23, 2020, now U.S. Pat. No. 11,370,767, issued Jun. 28, 2022, which claims the benefit under 35 U.S.C. § 119(e) of U.S. Provisional Patent Application Ser. No. 62/837,613, filed Apr. 23, 2019, the disclosure of each of which is hereby incorporated herein in its entirety by this reference.

TECHNICAL FIELD

The disclosure, in various embodiments, relates to *Cannabis* processing systems and methods. More specifically, embodiments of the disclosure relate to *Cannabis* processing systems and methods employing disruption of cell walls of wet *Cannabis* particles through one or more of flash freezing, cellulose solvent exposure, applied negative pressure, and vacuum distillation.

BACKGROUND

*Cannabis* is a genus of plants in the family Cannabaceae. Acknowledged *Cannabis* species include *Cannabis sativa*, *Cannabis* indica and *Cannabis ruderalis*. *Cannabis* plants include numerous (400+) cannabinoids ($C_{21}$ terpenophenolic compounds), some of which can provide therapeutic and medicinal benefits. For example, different cannabinoids have been utilized to treat various conditions, such as pain, nausea, seizures, convulsions, vomiting, lack of appetite, inflammation, psychosis, arthritis, cancer, and other conditions. In addition, different cannabinoids have been used to provide various desired effects, such as psychoactive effects, neuroprotective effects, and immunomodulatory effects. To date, eighty-five (85) cannabinoids have been isolated from *Cannabis* plants.

Unfortunately, conventional systems and methods of processing *Cannabis* to obtain desirable cannabinoids therefrom suffer from a variety of disadvantages. For example, one conventional method of processing *Cannabis* to obtain desirable cannabinoids therefrom includes drying harvested, wet portions of *Cannabis* plants to a moisture content of less than fifteen (15) percent, shredding the dried portions of the *Cannabis* plants to form dry *Cannabis* particles (e.g., a powder of dry *Cannabis* particles), and then extracting desired cannabinoids from the dry *Cannabis* particles using an extraction agent (e.g., an extraction solvent). Drying the harvested portions of the *Cannabis* plants ruptures cell walls of the plant cells thereof to permit the extraction of cannabinoids within the plant cells using the extraction agent. However, the drying process can be undesirably long (e.g., weeks) and/or require costly and energy-intensive equipment (e.g., heating apparatuses) and personnel to expedite the process. In addition, other conventional methods of processing *Cannabis* that forego the drying process and treat harvested, wet portions of *Cannabis* plants with an extraction agent generally have undesirably low cannabinoid product yields, such as less than or equal to about 50 percent.

Accordingly, there is a need for new *Cannabis* processing systems and methods that are fundamentally different than conventional technologies.

BRIEF SUMMARY

Embodiments described herein include *Cannabis* processing systems and methods of processing *Cannabis*. In accordance with one embodiment described herein, a *Cannabis* processing system comprises a grinding apparatus and a cell disruption apparatus. The grinding apparatus is configured to grind wet *Cannabis* cuttings to form a ground, wet *Cannabis* material comprising wet *Cannabis* particles having an average particle size within a range of from about 1 mm to about 3 mm. The cell disruption apparatus is downstream of the grinding apparatus and is configured to disrupt cell walls of plant cells of the wet *Cannabis* particles through one or more of flash freezing, a cellulose solvent, applied negative pressure, and vacuum distillation to facilitate removal of one or more cannabinoids within the plant cells of the wet *Cannabis* particles.

In additional embodiments, a method of processing *Cannabis* comprises mechanically breaking down wet *Cannabis* cuttings to form a *Cannabis* material comprising wet *Cannabis* particles. Cell walls of the wet *Cannabis* particles are disrupted using one or more of flash freezing, a cellulose solvent, negative pressure, and vacuum distillation.

In yet additional embodiments, a method of processing *Cannabis* comprises grinding harvested portions of one or more *Cannabis* plants to form a ground *Cannabis* material comprising discrete *Cannabis* particles having an average particle size within a range of from about 1 mm to about 3 mm. The ground *Cannabis* material is subjected to one or more of a flash freezing process, treatment with a cellulose solvent, exposure to negative pressure, and a vacuum distillation process to facilitate access to one or more cannabinoids contained within plant cells.

BRIEF DESCRIPTION OF THE DRAWINGS

FIGS. 7A through 9B are tables showing the results of analysis performed on the cannabinoid separation subsystem shown in FIG. 6 using different cannabinoid extraction solvents, as described in Example 4.

DETAILED DESCRIPTION

Figure 1:
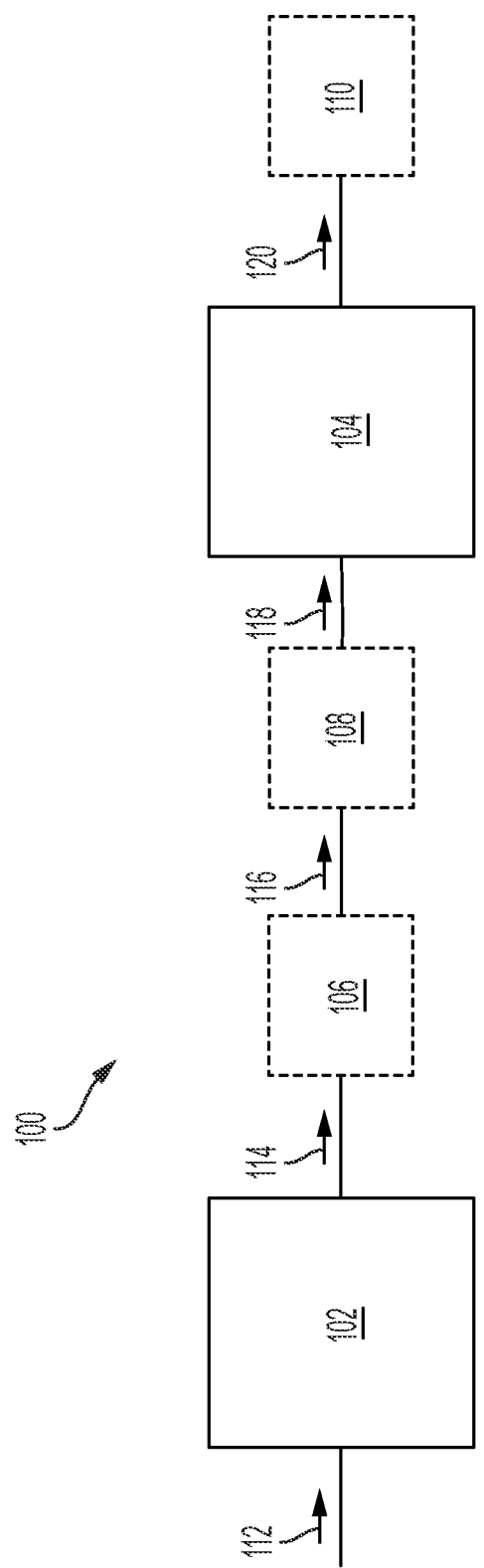
FIG. 1 is a simplified schematic view of a *Cannabis* processing system, in accordance with an embodiment of the disclosure.

The following description provides specific details, such as chemical compositions and processing conditions (e.g., temperatures, pressures, cooling rates, etc.) in order to provide a thorough description of embodiments of the disclosure. However, a person of ordinary skill in the art will understand that the embodiments of the disclosure may be practiced without necessarily employing these specific details. Indeed, the embodiments of the disclosure may be practiced in conjunction with conventional systems and methods employed in the industry. In addition, only those process components and acts necessary to understand the embodiments of the present disclosure are described in detail below. A person of ordinary skill in the art will understand that some process components (e.g., pipelines, line filters, valves, temperature detectors, flow detectors, pressure detectors, and the like) are inherently disclosed herein and that adding various conventional process components and acts would be in accord with the disclosure. In addition, the drawings accompanying the application are for illustrative purposes only and are not meant to be actual views of any particular material, device, or system. Moreover, elements in common between figures may retain the same numerical designation.

As used herein, the terms "comprising," "including," "containing," "having," and grammatical equivalents thereof are inclusive or open-ended terms that do not exclude additional, unrecited elements or method acts, but also include the more restrictive terms "consisting of" and "consisting essentially of" and grammatical equivalents thereof. As used herein, the term "may" with respect to a material, structure, feature, or method act indicates that such is contemplated for use in implementation of an embodiment of the disclosure and such term is used in preference to the more restrictive term "is" so as to avoid any implication that other, compatible materials, structures, features and methods usable in combination therewith should or must be, excluded.

As used herein, the singular forms "a," "an," and "the" are intended to include the plural forms as well, unless the context clearly indicates otherwise.

As used herein, "and/or" includes any and all combinations of one or more of the associated listed items.

As used herein, the term "configured" refers to a size, shape, material composition, orientation, and arrangement of one or more of at least one structure and at least one apparatus facilitating operation of one or more of the structure and the apparatus in a pre-determined way.

As used herein, the term "substantially" in reference to a given parameter, property, or condition means and includes to a degree that one of ordinary skill in the art would understand that the given parameter, property, or condition is met with a degree of variance, such as within acceptable tolerances. By way of example, depending on the particular parameter, property, or condition that is substantially met, the parameter, property, or condition may be at least 90.0 percent met, at least 95.0 percent met, at least 99.0 percent met, at least 99.9 percent met, or even 100.0 percent met.

As used herein, "about" or "approximately" in reference to a numerical value for a particular parameter is inclusive of the numerical value and a degree of variance from the numerical value that one of ordinary skill in the art would understand is within acceptable tolerances for the particular parameter. For example, "about" or "approximately" in reference to a numerical value may include additional numerical values within a range of from 90.0 percent to 110.0 percent of the numerical value, such as within a range of from 95.0 percent to 105.0 percent of the numerical value, within a range of from 97.5 percent to 102.5 percent of the numerical value, within a range of from 99.0 percent to 101.0 percent of the numerical value, within a range of from 99.5 percent to 100.5 percent of the numerical value, or within a range of from 99.9 percent to 100.1 percent of the numerical value.

An embodiment of the disclosure will now be described with reference to FIG. 1, which schematically illustrates a *Cannabis* processing system 100. The *Cannabis* processing system 100 may be used to process wet *Cannabis* cuttings to access and extract one or more cannabinoids contained within plant cells thereof, which may then be removed (e.g., separated) from other chemical compounds (e.g., non-cannabinoid compounds, such as esters, terpenes, water; other cannabinoids) of the wet *Cannabis* cuttings. As a non-limiting example, the *Cannabis* processing system 100 may be used to access and extract, from the plant cells of the wet *Cannabis* cuttings, one or more of tetrahydrocannabinol (THC), delta-8-THC, tetrahydrocannabinolic acid (THCA), tetrahydrocannabivarin (THCV), tetrahydrocannabivarinic acid (THCVA), cannabidiol (CBD), cannabidiolic acid (CBDA), cannabidivarin (CBDV), cannabidivarinic acid (CBDVA), cannabinol (CBN), cannabinolic acid (CBNA), cannabavarin (CBV), cannabavarinic acid (CBVA), cannabigerol (CBG), cannabigerolic acid (CBGA), cannabigerovarin (CBGV), cannabigerovarinic acid (CBGVA), cannabinidiol (CBND), cannabinidiolic acid (CBNDA), cannabichromene (CBC), cannabichromenic acid (CBCA), cannabichromevarin (CBCV), cannabichromevarinic acid (CBCVA), cannabicyclol (CBL), cannabicyclolic acid (CBLA), cannabitriol (CBT), cannabitriolic acid (CBTA), cannabielsoin (CBE), and cannabielsoinic acid (CBEA), and cannabigerol monomethyl ether (CBGM). As used herein, THC, THCV, CBD, CBDV, CBN, CBV, CBG, CBGV, CBND, CBC, CBCV, CBL, CBT, CBE, and CBGM refer to the decarboxylated form of the cannabinoid; and THCA, THCVA, CBDA, CBNA, CBVA, CBGA, CBGVA, CBNDA, CBCA, CBCVA, CBLA, CBTA, and CBEA refer to the acid form of the cannabinoid. As another non-limiting example, the *Cannabis* processing system 100 may be used to access and extract, from the plant cells of the wet *Cannabis* cuttings, one or more terpenes.

As used herein, "wet *Cannabis* cuttings" means and includes harvested portions (e.g., cuttings, trimmings, pickings, pluckings) of one or more *Cannabis* plants including at least about fifteen (15) percent of the water present within the harvested portions at the time of harvesting. The wet *Cannabis* cuttings may include one or more of buds, flowers, leaves, stems, and trichomes of the *Cannabis* plants. The wet *Cannabis* cuttings may include greater than or equal to about 15 percent of the water present in the harvested portions of the *Cannabis* plants at the time of harvesting, such as greater than or equal to about 25 percent of the water, greater than or equal to about 50 percent of the water, greater than or equal to about 75 percent of the water, greater than or equal to about 85 percent of the water, greater than or equal to about 95 percent of the water, or even about 100 percent of the water. In some embodiments, the wet *Cannabis* cuttings include a majority (e.g., greater than 50 percent) of the water present in the harvested portions of the *Cannabis* plants at the time of harvesting.

As shown in FIG. 1, the *Cannabis* processing system 100 may include at least one grinding apparatus 102 and at least one cell disruption apparatus 104 downstream of the grinding apparatus 102. Optionally, as described in further detail below, the *Cannabis* processing system 100 may also include one or more of a mechanical dewatering apparatus 106 downstream of the grinding apparatus 102 and upstream of the cell disruption apparatus 104; a wetting apparatus 108 downstream of the mechanical dewatering apparatus 106 and/or the grinding apparatus 102 and upstream of the cell disruption apparatus 104; and a separation apparatus 110 downstream of the cell disruption apparatus 104.

The grinding apparatus 102 may comprise at least one apparatus configured and operated to receive a wet *Cannabis* feed 112 including wet *Cannabis* cuttings and to mechanically break down (e.g., grind, shred, chip, rend) the wet *Cannabis* cuttings to form a ground, wet *Cannabis* material 114 including relatively smaller, discrete wet *Cannabis* particles (e.g., segments, pieces, parts) having a predetermined average particle size suitable for subsequent operations (e.g., cell disruption operations, cannabinoid extraction operations) of the *Cannabis* processing system 100. The predetermined average particle size of the discrete wet

*Cannabis* particles may be large enough to limit release (e.g., liberation) of desirable cannabinoids into intercellular liquid (e.g., intercellular water) of the ground, wet *Cannabis* material 114, and small enough to facilitate desirable interactions between one or more solvents (e.g., cannabinoid extraction solvents; other solvents, such as cellulose solvent) and *Cannabis* plant cells. By way of non-limiting example, the grinding apparatus 102 may be configured and operated to mechanically break down the wet *Cannabis* cuttings of the wet *Cannabis* feed 112 into discrete wet *Cannabis* particles having an average particle size within a range of from about 0.5 millimeter (mm) to about 5 mm, such as from about 1 mm to about 3 mm. Particle sizes of wet *Cannabis* particles may be determined by conventional processes, such as conventional laser diffraction processes and conventional wet sieving processes. For example, particle sizes of wet *Cannabis* particles may be determined using a conventional wet sieving process employing mesh numbers 3½ through 40. In some embodiments, the grinding apparatus 102 is configured to grind (e.g., shred, rend) wet *Cannabis* cuttings of the wet *Cannabis* feed 112 into discrete wet *Cannabis* particles each individually exhibiting a size within a range of from about 1 mm to about 3 mm, as determined by a wet sieving process employing mesh numbers 6 through 20.

The grinding apparatus 102 may exhibit any configuration capable of mechanically breaking down the wet *Cannabis* cuttings into wet *Cannabis* particles having desired sizes (e.g., sizes within a range of from about 1 mm to about 3 mm). By way of non-limiting example, the grinding apparatus 102 may comprise one or more of a grinding roller (e.g., a low speed, high-torque grinding roller, such as a low speed, high-torque dual shafted grinder), a disc chipper, a drum chipper, a tub grinder, a ball mill, and a hammer mill. The grinding apparatus 102 may, optionally, include one or more structures (e.g., screens) configured with an appropriate mesh or other aperture sizing and positioned to ensure that wet *Cannabis* particles exiting the grinding apparatus 102 are within a predetermined particle size range (e.g., within a range of from about 1 mm to about 3 mm).

Although the *Cannabis* processing system 100 is depicted as including a single (e.g., only one) grinding apparatus 102 in FIG. 1, the *Cannabis* processing system 100 may include any number of grinding apparatuses 102. The number of grinding apparatuses 102 included in the *Cannabis* processing system 100 may at least partially depend on a desired output of material(s) for further processing (including recovery of spent (fully extracted) material(s) for use in extracting or producing materials from waste streams). Put another way, the *Cannabis* processing system 100 may include a single (e.g., only one) grinding apparatus 102, or may include multiple (e.g., more than one) grinding apparatuses 102. If the *Cannabis* processing system 100 includes multiple grinding apparatuses 102, each of the grinding apparatuses 102 may be substantially the same (e.g., exhibit substantially the same components, component sizes, component shapes, component material compositions, component material distributions, component positions, component orientations, etc.) and may be operated under substantially the same conditions (e.g., feed rates, grinder speed, grinder torque, etc.), or at least one of the grinding apparatuses 102 may be different (e.g., exhibit one or more of different components, different component sizes, different component shapes, different component material compositions, different component material distributions, different component positions, different component orientations, etc.) than at least one other of the grinding apparatuses 102 and/or may be operated under different conditions (e.g., a different feed rate, a different grinder speed, a different grinder torque, etc.) than at least one other of the grinding apparatuses 102. In some embodiments, two of more grinding apparatuses 102 are provided in parallel with one another. In additional embodiments, two of more grinding apparatuses 102 are provided in series with one another.

With continued reference to FIG. 1, if present, the mechanical dewatering apparatus 106 may comprise at least one apparatus configured and operated to receive and partially (e.g., less than completely) mechanically remove excess water from the ground, wet *Cannabis* material 114 exiting the grinding apparatus 102 to form a partially dewatered *Cannabis* material 116. The mechanical dewatering apparatus 106 may be configured and operated to substantially remove intercellular water of the ground, wet *Cannabis* material 114 while substantially maintaining intracellular water of the ground, wet *Cannabis* material 114. In some embodiments, the mechanical dewatering apparatus 106 is configured and operated to remove from about 75 percent to about 95 percent of intercellular water present within the ground, wet *Cannabis* material 114, such as from about 80 percent to about 90 percent of the intercellular water present within the ground, wet *Cannabis* material 114. The water content of the ground, wet *Cannabis* material 114 and the partially dewatered *Cannabis* material 116 may be determined using conventional moisture measurement processes and equipment, such as one or more conventional volumetric moisture sensors.

The mechanical dewatering apparatus 106, if any, may exhibit any configuration capable of partially mechanically dewatering the ground, wet *Cannabis* material 114. By way of non-limiting example, the grinding apparatus 102 may comprise one or more of a pressing apparatus (e.g., a roller press, such as a cold roller press), a filtration apparatus (e.g., a vacuum filtration apparatus), and a centrifuge apparatus. In some embodiments, the mechanical dewatering apparatus 106 is a roller press. The roller press may, for example, press the ground, wet *Cannabis* material 114 between one or more pairs of rollers to partially dewater and reduce a thickness of the ground, wet *Cannabis* material 114. The roller press may produce one or more sheet structures comprising a partially dewatered *Cannabis* material including the discrete wet *Cannabis* particles of the ground, wet *Cannabis* material 114. In additional embodiments, the mechanical dewatering apparatus 106 is a vacuum filtration apparatus configured and operated to apply negative pressure to the ground, wet *Cannabis* material 114 to remove intercellular water of the ground, wet *Cannabis* material 114 and form the partially dewatered *Cannabis* material 116.

The *Cannabis* processing system 100 may include any number of mechanical dewatering apparatuses 106, such as a single (e.g., only one) mechanical dewatering apparatus 106, multiple (e.g., more than one) mechanical dewatering apparatuses 106, or no mechanical dewatering apparatuses 106. If the *Cannabis* processing system 100 includes multiple mechanical dewatering apparatuses 106, each of the mechanical dewatering apparatuses 106 may be substantially the same and may be operated under substantially the same conditions, or at least one of the mechanical dewatering apparatuses 106 may be different than at least one other of the mechanical dewatering apparatuses 106 and/or may be operated under different conditions than at least one other of the mechanical dewatering apparatuses 106. In some embodiments, two of more mechanical dewatering apparatuses 106 are provided in parallel with one another. In additional embodiments, two of more mechanical dewatering apparatuses 106 are provided in series with one another.

With continued reference to FIG. 1, if present, the wetting apparatus 108 may comprise at least one apparatus configured and operated to wet the partially dewatered *Cannabis* material 116 exiting the mechanical dewatering apparatus 106 (if any) (or the ground, wet *Cannabis* material 114 exiting the grinding apparatus 102) with at least one cannabinoid extraction solvent (e.g., a cannabinoid extraction solvent to be employed in a subsequent extraction step) to form a wetted *Cannabis* material 118. The cannabinoid extraction solvent may, for example, comprise one or more of acetone, acetonitrile, butane, 1-butanol, 2-butanol, dichloromethane, diethyl ether, ethanol, ethyl acetate, hexane, heptane, isopropyl acetate, methanol, isopropanol, isopropyl ether, and methyl tert-butyl ether. In some embodiments, the cannabinoid extraction solvent is ethanol. The wetting apparatus 108 may be configured and operated to add enough cannabinoid extraction solvent to the partially dewatered *Cannabis* material 116 to facilitate a weight ratio of solids to liquids within the wetted *Cannabis* material 118 within a range of from about 2:1 to about 5:1.

The wetting apparatus 108, if any, may exhibit any configuration capable of wetting the partially dewatered *Cannabis* material 116 (or the ground, wet *Cannabis* material 114) with the cannabinoid extraction solvent. By way of non-limiting example, the wetting apparatus 108 may comprise a spray chamber apparatus configured to receive the partially dewatered *Cannabis* material 116 and the cannabinoid extraction solvent, and to form and direct (e.g., spray) discrete portions (e.g., drops, aerosol) of the cannabinoid extraction solvent onto to the partially dewatered *Cannabis* material 116.

In some embodiments, the wetting apparatus 108, if any, is configured and operated to add cooled cannabinoid extraction solvent to the partially dewatered *Cannabis* material 116. The cannabinoid extraction solvent may, for example, be cooled (e.g., supercooled) to a temperature near the freezing temperature of the cannabinoid extraction solvent. By way of non-limiting example, the cannabinoid extraction solvent may be cooled to a temperature within 20° C. (e.g., within 10° C., within 5° C., within 2.5° C., or within 1° C.) of the freezing temperature of the cannabinoid extraction solvent. Wetting the partially dewatered *Cannabis* material 116 with a cooled (e.g., supercooled) cannabinoid extraction solvent may enhance thermal transfer properties of the wetted *Cannabis* material 118 relative to the partially dewatered *Cannabis* material 116 to enhance the efficiency of subsequent cell disruption operations (e.g., flash freezing operations, if employed) using the cell disruption apparatus 104, as described in further detail below. The cannabinoid extraction solvent may be cooled within the wetting apparatus 108 and/or may be cooled outside of the wetting apparatus 108 (e.g., using one or more heat transfer apparatuses) and delivered to the wetting apparatus 108.

The *Cannabis* processing system 100 may include any number of wetting apparatuses 108, such as a single (e.g., only one) wetting apparatus 108, multiple (e.g., more than one) wetting apparatuses 108, or no wetting apparatuses 108. If the *Cannabis* processing system 100 includes multiple wetting apparatuses 108, each of the wetting apparatuses 108 may be substantially the same and may be operated under substantially the same conditions, or at least one of the wetting apparatuses 108 may be different than at least one other of the wetting apparatuses 108 and/or may be operated under different conditions than at least one other of the wetting apparatuses 108. In some embodiments, two of more wetting apparatuses 108 are provided in parallel with one another. In additional embodiments, two of more wetting apparatuses 108 are provided in series with one another.

With continued reference to FIG. 1, the cell disruption apparatus 104 comprises at least one apparatus configured and operated to at a least partially (e.g., substantially) disrupt (e.g., break down) cell walls of plant cells of the wet *Cannabis* particles produced by the grinding apparatus 102. Disrupting the cell walls of the plant cells of the wet *Cannabis* particles may facilitate the access to one or more cannabinoids within the plants cells, such as cannabinoids attached to intracellular surfaces of the plant cells, to permit removal (e.g., extraction) of the cannabinoids using one or more additional processing acts (e.g., one or more cannabinoid extraction acts). Disrupting the cell walls of the plant cells of the wet *Cannabis* particles may also directly effectuate the release (e.g., liberation, detachment) of one or more cannabinoids from surfaces (e.g., intracellular surfaces, intercellular surfaces) the plant cells, such as inner surfaces and/or outer surfaces of the cell walls of the plant cells.

As shown in FIG. 1, the cell disruption apparatus 104 may receive the ground, wet *Cannabis* material 114 from the grinding apparatus 102, the partially dewatered *Cannabis* material 116 from the mechanical dewatering apparatus 106 (if any), or the wetted *Cannabis* material 118 from the wetting apparatus 108 (if any), and may disrupt the cell walls of plant cells of the wet *Cannabis* particles thereof to produce a cellularly-disrupted *Cannabis* effluent 120. As described in further detail below, the cell disruption apparatus 104 may be configured and operated to subject the wet *Cannabis* particles to one or more of flash freezing, contact with at least one cellulose solvent, and one or more applied negative pressures to disrupt the cell walls of the plant cells thereof.

In some embodiments, the cell disruption apparatus 104 comprises an apparatus configured and operated to subject the wet *Cannabis* particles produced by the grinding apparatus 102 to flash freezing to disrupt the cell walls of the plant cells of the wet *Cannabis* particles. The cell disruption apparatus 104 may, for example, be configured and operated to cool (e.g., rapidly cool) the wet *Cannabis* particles to a crystallization temperature sufficient to crystallize and expand intracellular fluid (e.g., intracellular water) of the plant cells, and then maintain the crystallization temperature until the intracellular fluid is substantially crystallized. The crystallization and expansion of the intracellular fluid of the plant cells may rupture the cell walls of the plant cells to facilitate access to cannabinoids contained within the intracellular space (e.g., on intracellular surfaces) of the plant cells. The cell disruption apparatus 104 may receive and cool the ground, wet *Cannabis* material 114, the partially dewatered *Cannabis* material 116 (if produced using the mechanical dewatering apparatus 106), or the wetted *Cannabis* material 118 (if produced using the wetting apparatus 108) to flash freeze the wet *Cannabis* particles produced by the grinding apparatus 102. In some embodiments, the cell disruption apparatus 104 receives and acts upon the wetted *Cannabis* material 118 from the grinding apparatus 102 (e.g., the mechanical dewatering apparatus 106 and the wetting apparatus 108, along with the processing acts associated therewith, are employed upstream of the cell disruption apparatus 104). The wetted *Cannabis* material 118 (or the ground, wet *Cannabis* material 114; or the partially dewatered *Cannabis* material 116) may, for example, comprise greater than or equal to about fifty (50) percent of the water present, at the time of harvesting, within the harvested portions of one or more *Cannabis* plants employed to form the wetted *Cannabis* material 118.

The parameters (e.g., crystallization temperature, cooling rate, cooling duration, cooling media) employed by the cell disruption apparatus 104 (e.g., flash freezing apparatus) to flash freeze the wet *Cannabis* particles may at least partially depend on the thermal mass of the material (e.g., the ground, wet *Cannabis* material 114, the partially dewatered *Cannabis* material 116, or the wetted *Cannabis* material 118) being received and acted upon by the cell disruption apparatus 104. The crystallization temperature, the cooling rate to reach to the crystallization temperature, and the period of time the crystallization temperature may be selected to promote expansion (and, hence, impede shrinking) of the intracellular fluid through the flash freezing process. In some embodiments, the crystallization temperature, the cooling rate to reach to the crystallization temperature, and the period of time that the crystallization temperature is maintained are selected to maximize the volume of crystalline material formed from the intracellular fluid through the flash freezing process. As a non-limiting example, in some embodiments (e.g., embodiments wherein the cell disruption apparatus 104 receives and acts upon the wetted *Cannabis* material 118) the crystallization temperature is selected to be within a range of from about −60° C. to about −80° C. (e.g., from about −70° C. to about −80° C.), the crystallization temperature is reached (e.g., starting from room temperature, such as from about 20° C. to about 22° C.) in less than or equal to about two (2) minutes (e.g., less than or equal to about one (1) minute, less than or equal to about 45 seconds, less than or equal to about 30 seconds, less than or equal to about 15 seconds), and the crystallization temperature is maintained for a period of time within a range of from about one (1) minute to about ten (10) minutes (e.g., from about one (1) minute to about five (5) minutes, from about one (1) minute to about three (3) minutes). In some embodiments, at least one cannabinoid extraction solvent (e.g., one or more of acetone, acetonitrile, butane, 1-butanol, 2-butanol, dichloromethane, diethyl ether, ethanol, ethyl acetate, hexane, heptane, isopropyl acetate, methanol, isopropanol, isopropyl ether, and methyl tert-butyl ether) cooled to the crystallization temperature is employed as a cooling media for the flash freezing process. The cannabinoid extraction solvent may, for example, be combined (e.g., mixed) with the wet *Cannabis* particles within the cell disruption apparatus 104. In further embodiments, a different cooling media (e.g., a cooling media other than a cannabinoid extraction solvent) is employed as a cooling media for the flash freezing process.

In additional embodiments, the cell disruption apparatus 104 comprises an apparatus configured and operated to treat the wet *Cannabis* particles produced by the grinding apparatus 102 with at least one cellulose solvent to disrupt the cell walls of the plant cells of the wet *Cannabis* particles. The cell disruption apparatus 104 may, for example, be configured and operated to contact (e.g., spray, coat, immerse) the wet *Cannabis* particles with the cellulose solvent for a sufficient period of time to dissolve cellulose of the cell walls of the plant cells of the wet *Cannabis* particles. Dissolving the cellulose of the cell walls may facilitate access to cannabinoids contained within the intracellular space (e.g., on intracellular surfaces) of the plant cells. Dissolving the cellulose of the cell walls may also free (e.g., liberate, detach, unbind) cannabinoids attached to and/or contained within the cell walls, such as cannabinoids attached to surfaces (e.g., inner surfaces, outer surfaces) of the cell walls. The cell disruption apparatus 104 may receive and treat the ground, wet *Cannabis* material 114, the partially dewatered *Cannabis* material 116 (if produced using the mechanical dewatering apparatus 106), or the wetted *Cannabis* material 118 (if produced using the wetting apparatus 108) with the cellulose solvent to disrupt the cell walls of the plant cells of the wet *Cannabis* particles produced by the grinding apparatus 102. In some embodiments, the cell disruption apparatus 104 receives and treats the ground, wet *Cannabis* material 114 from the grinding apparatus 102 (e.g., the mechanical dewatering apparatus 106 and the wetting apparatus 108, along with the processing acts associated therewith, are not employed upstream of the cell disruption apparatus 104). The ground, wet *Cannabis* material 114 (or the partially dewatered *Cannabis* material 116; or the wetted *Cannabis* material 118) may, for example, comprise greater than or equal to about fifteen (15) percent of the water present, at the time of harvesting, within the harvested portions of one or more *Cannabis* plants employed to form the ground, wet *Cannabis* material 114.

If a cellulose solvent is used to disrupt the cell walls of plant cells of the wet *Cannabis* particles produced by the grinding apparatus 102, the cell disruption apparatus 104 may exhibit any configuration capable of treating the wet *Cannabis* particles with the cellulose solvent. By way of non-limiting example, the cell disruption apparatus 104 may comprise a spray chamber apparatus configured to receive the ground, wet *Cannabis* material 114 (or the partially dewatered *Cannabis* material 116, or the wetted *Cannabis* material 118) and the cellulose solvent, and to form and direct (e.g., spray) discrete portions (e.g., drops, aerosol) of the cellulose solvent onto to the ground, wet *Cannabis* material 114 (or the partially dewatered *Cannabis* material 116, or the wetted *Cannabis* material 118).

The cell disruption apparatus 104 may utilize a cellulose extract solvent (if any) able to dissolve cellulose of the cell walls of the plant cells of the wet *Cannabis* particles without modifying the chemical structures of desirable cannabinoids (e.g., THC, CBD, etc.) of the wet *Cannabis* particles. The cellulose extract solvent may also be selected to be readily separable from the desirable cannabinoids. In addition, the cellulose extract solvent may be selected to be relatively non-hazardous (e.g., non-toxic) and environmentally friendly. By way of non-limiting example, the cellulose extract solvent (if any) may comprise one or more of 4-methylmorpholine 4-oxide (NMMO), an ionic liquid, dimethylsulfoxide (DMSO), paraformaldehyde (PFA), dimethylformamide (DMF), and dimethylacetamide (DMAc). Furthermore, the cellulose extract solvent (if any) may be combined with (e.g., added to) the ground, wet *Cannabis* material 114 (or the partially dewatered *Cannabis* material 116, or the wetted *Cannabis* material 118) under any desirable conditions (e.g., temperatures, pressures) able to maintain the chemical structure(s) of the desirable cannabinoid(s) of the wet *Cannabis* particles.

In further embodiments, the cell disruption apparatus 104 comprises an apparatus configured and operated to apply negative pressure to the wet *Cannabis* particles produced by the grinding apparatus 102 to disrupt the cell walls of the plant cells of the wet *Cannabis* particles. The cell disruption apparatus 104 may, for example, be configured and operated to subject the wet *Cannabis* particles to applied negative pressure within a range of from about −2 pounds per square inch gauge (psig) to about −10 psig. Applying negative pressure to the wet *Cannabis* particles may rupture the cell walls of the plant cells to facilitate access to cannabinoids contained within the intracellular space (e.g., on intracellular surfaces) of the plant cells. The cell disruption apparatus 104 may receive and apply negative pressure to the ground, wet *Cannabis* material 114, the partially dewatered *Cannabis* material 116 (if produced using the mechanical dewatering apparatus 106), or the wetted *Cannabis* material 118 (if produced using the wetting apparatus 108) to act upon the wet *Cannabis* particles produced by the grinding apparatus 102. In some embodiments, the cell disruption apparatus 104 receives and applies negative pressure to the ground, wet *Cannabis* material 114 from the grinding apparatus 102 (e.g., the mechanical dewatering apparatus 106 and the wetting apparatus 108, along with the processing acts associated therewith, are not employed upstream of the cell disruption apparatus 104). The ground, wet *Cannabis* material 114 (or the partially dewatered *Cannabis* material 116; or the wetted *Cannabis* material 118) may, for example, comprise greater than or equal to about twenty-five (25) percent of the water present, at the time of harvesting, within the harvested portions of one or more *Cannabis* plants employed to form the ground, wet *Cannabis* material 114.

In still further embodiments, the cell disruption apparatus 104 comprises an apparatus configured and operated to subject the wet *Cannabis* particles produced by the grinding apparatus 102 to a vacuum distillation process to disrupt the cell walls of the plant cells of the wet *Cannabis* particles. Subjecting the wet *Cannabis* particles to the vacuum distillation process may rupture the cell walls of the plant cells to facilitate access to cannabinoids contained within the intracellular space (e.g., on intracellular surfaces) of the plant cells. The vacuum distillation process may also separate different chemical compounds (e.g., different non-cannabinoid compounds, such as terpenes, esters, water, etc.; different cannabinoid compounds, such as CBD, THC; etc.) of the wet *Cannabis* particles from one another based on differences in the volatilities thereof, as described in further detail below. The cell disruption apparatus 104 may receive and act upon the ground, wet *Cannabis* material 114, the partially dewatered *Cannabis* material 116 (if produced using the mechanical dewatering apparatus 106), or the wetted *Cannabis* material 118 (if produced using the wetting apparatus 108) to subject the wet *Cannabis* particles produced by the grinding apparatus 102 to vacuum distillation. In some embodiments, the cell disruption apparatus 104 receives and subjects the ground, wet *Cannabis* material 114 from the grinding apparatus 102 to vacuum distillation (e.g., the mechanical dewatering apparatus 106 and the wetting apparatus 108, along with the processing acts associated therewith, are not employed upstream of the cell disruption apparatus 104). The ground, wet *Cannabis* material 114 (or the partially dewatered *Cannabis* material 116; or the wetted *Cannabis* material 118) may, for example, comprise greater than or equal to about twenty-five (25) percent of the water present, at the time of harvesting, within the harvested portions of one or more *Cannabis* plants employed to form the ground, wet *Cannabis* material 114.

If employed, the vacuum distillation process facilitated by the cell disruption apparatus 104 may include subjecting the wet *Cannabis* particles to increasingly negative pressures to rupture the cell walls of the plant cells of the wet *Cannabis* particles and boil off different chemical compounds of the wet *Cannabis* particles at different times. The vacuum distillation process may, for example, gradually increase negative pressures applied to the wet *Cannabis* particles up to about $10^{-3}$ pounds per square inch absolute (psia). In some embodiments, the vacuum distillation process subjects the wet *Cannabis* particles to increasingly negative pressures within a range of from about −4 psig to about $10^{-3}$ psia (e.g., from about −2 psig to about $10^{-3}$ psia). The different chemical compounds of the wet *Cannabis* particles may be boiled off and separated from one another based on their relative volatilities, with relatively more volatile chemical compounds being boiled off earlier and at relatively lower negative pressures, and relatively less volatile chemical compounds being boiled off later and at relatively higher negative pressures. By way of non-limiting example, terpenes, esters, and water of the wet *Cannabis* particles may be boiled off (e.g., sequentially, simultaneously, a combination thereof) at one or more negative pressures, and then one or more cannabinoids (e.g., CBD, THC, CBA, CBG, CBH) of the wet *Cannabis* particles may be boiled off (e.g., sequentially, simultaneously, a combination thereof) at one or more relatively greater negative pressures. In some embodiments, terpenes and esters of the wet *Cannabis* particles are boiled off at one or more relatively lower negative pressures, followed by water of the wet *Cannabis* particles at a relatively higher negative pressure, followed by CBD of the wet *Cannabis* particles at a relatively higher negative pressure, followed by one or more (e.g., each) of THC, CBA, CBG, and CBH of the wet *Cannabis* particles at one or more relatively higher negative pressures. Optionally, the wet *Cannabis* particles may be heated to assist with boiling off one or more chemical compounds of the wet *Cannabis* particles, such as one or more chemical compounds having relatively lower volatilities. By way of non-limiting example, the wet *Cannabis* particles may be heated to a temperature within a range of from about 25° C. to about 75° C., such as from about 35° C. to about 65° C., or from about 40° C. to about 60° C.

Although the *Cannabis* processing system 100 is depicted as including a single (e.g., only one) cell disruption apparatus 104 in FIG. 1, the *Cannabis* processing system 100 may include any number of cell disruption apparatuses 104. Put another way, the *Cannabis* processing system 100 may include a single (e.g., only one) cell disruption apparatus 104, or may include multiple (e.g., more than one) cell disruption apparatuses 104. If the *Cannabis* processing system 100 includes multiple cell disruption apparatuses 104, each of the cell disruption apparatuses 104 may be substantially the same (e.g., exhibit substantially the same components, component sizes, component shapes, component material compositions, component material distributions, component positions, component orientations, etc.) and may be operated under substantially the same conditions, or at least one of the cell disruption apparatuses 104 may be different (e.g., exhibit one or more of different components, different component sizes, different component shapes, different component material compositions, different component material distributions, different component positions, different component orientations, etc.) than at least one other of the cell disruption apparatuses 104 and/or may be operated under different conditions than at least one other of the cell disruption apparatuses 104. In some embodiments, two of more cell disruption apparatuses 104 are provided in parallel with one another. In additional embodiments, two of more cell disruption apparatuses 104 are provided in series with one another.

With continued reference to FIG. 1, if present, the separation apparatus 110 may comprise at least one apparatus configured and operated to separate one or more components of the cellularly-disrupted *Cannabis* effluent 120 exiting the cell disruption apparatus 104 from one another. By way of non-limiting example, if present, the separation apparatus 110 may be configured and operated to separate (e.g., extract) one or more desirable cannabinoids of the cellularly-disrupted *Cannabis* effluent 120 from one or more other chemical compounds of the cellularly-disrupted *Cannabis* effluent 120 (e.g., one or more non-cannabinoid compounds, one or more undesirables cannabinoids). The configuration and use of the separation apparatus 110, if any, may at least partially dependent on the configuration and use of the cell disruption apparatus 104.

In some embodiments, such as some embodiments wherein the cell disruption apparatus 104 is configured and operated to flash freeze or apply negative pressure to the wet *Cannabis* particles produced by the grinding apparatus 102, the separation apparatus 110 is at least one extraction apparatus configured and operated to receive and combine (e.g., mix) the cellularly-disrupted *Cannabis* effluent 120 with at least one cannabinoid extraction solvent to dissolve one or more desirable cannabinoids of the cellularly-disrupted *Cannabis* effluent 120 and form a cannabinoid solution. The cannabinoid solution may then be removed from other components of the cellularly-disrupted *Cannabis* effluent 120 (e.g., in at least one other separation apparatus 110, such as a filtration apparatus), and the cannabinoid extraction solvent thereof may be driven off (e.g., in at least one additional separation apparatus 110, such one or more of an evaporation apparatus and a distillation apparatus), leaving the one or more desirable cannabinoids.

In additional embodiments, such as some embodiments wherein the cell disruption apparatus 104 is configured and operated to interact the wet *Cannabis* particles produced by the grinding apparatus 102 with at least one cellulose solvent, the cellulose solvent and dissolved cellulose of the cellularly-disrupted *Cannabis* effluent 120 is separated from the other components of the cellularly-disrupted *Cannabis* effluent 120 using at least one separation apparatus 110. The separation apparatus 110 may, for example, employ one or more of heat distillation, temperature-based separation (e.g., winterization), and vacuum distillation to separate the cellulose solvent and dissolved cellulose of the cellularly-disrupted *Cannabis* effluent 120 from the other components of the cellularly-disrupted *Cannabis* effluent 120. Thereafter, one or more remaining, desirable cannabinoids of the cellularly-disrupted *Cannabis* effluent 120 may be separated from other, remaining components of the cellularly-disrupted *Cannabis* effluent 120 in the manner previously described (e.g., using one or more additional separation apparatuses 110, such as an extractor apparatus, a filtration apparatus, and an evaporation apparatus).

In further embodiments, such as some embodiments wherein the cell disruption apparatus 104 is configured and operated to subject the wet *Cannabis* particles produced by the grinding apparatus 102 to vacuum distillation, one or more desirable cannabinoids exiting the cell disruption apparatus 104 are already sufficiently separated from other chemical compounds exiting the cell disruption apparatus 104 (e.g., at different times than the desirable cannabinoid(s)), and the separation apparatus 110 is omitted. In additional embodiments, the separation apparatus 110 may employ vacuum distillation to separate desirable cannabinoids from *Cannabis* particles. In some such embodiment, the separation apparatus 110 is without previously disrupting the *Cannabis* particles using a separate cell disruption apparatus 104. As a non-limiting example, the separation apparatus 110 may be employed to separate one or more desirable cannabinoids within the *Cannabis* particles (e.g., wet *Cannabis* particles and/or dry *Cannabis* particles) without previously treating the *Cannabis* particles using a separate cell disruption apparatus 104.

The *Cannabis* processing system 100 may include any number of separation apparatus 110 downstream of the cell disruption apparatus 104, such as a single (e.g., only one) separation apparatus 110, multiple (e.g., more than one) separation apparatus 110, or no separation apparatus 110. If the *Cannabis* processing system 100 includes multiple separation apparatuses 110 downstream of the cell disruption apparatus 104, each of the wetting apparatuses 108 may be substantially the same and may be operated under substantially the same conditions, or at least one of the multiple separation apparatuses 110 may be different than at least one other of the separation apparatuses 110 and/or may be operated under different conditions than at least one other of the separation apparatuses 110. In some embodiments, two of more multiple separation apparatuses 110 are provided in parallel with one another. In additional embodiments, two of more multiple separation apparatuses 110 are provided in series with one another.

The systems and methods of the disclosure may provide enhanced efficiency, reduced costs, and increase yield as compared to conventional *Cannabis* processing systems and methods. For example, the systems (e.g., the *Cannabis* processing system 100) and methods of the disclosure facilitate the simple processing of wet *Cannabis* cuttings to remove desirable cannabinoids therefrom, saving significant time, labor, and expense as compared to conventional systems and methods of processing *Cannabis* that require drying out wet *Cannabis* cuttings prior to further processing thereof. In addition, the systems and methods of the disclosure may facilitate increased cannabinoid product yield compared to conventional systems and methods of processing wet *Cannabis* cuttings, and may facilitate cannabinoid product yields at least as good as (or better than) those facilitated by conventional systems and methods of processing dried *Cannabis* cuttings.

The following examples serve to explain embodiments of the disclosure in more detail. These examples are not to be construed as being exhaustive, exclusive, or otherwise limiting as to the scope of the disclosure.

EXAMPLES

Example 1: Plant Cell Damage from Breakdown of Wet *Cannabis* Cuttings

Figure 2:
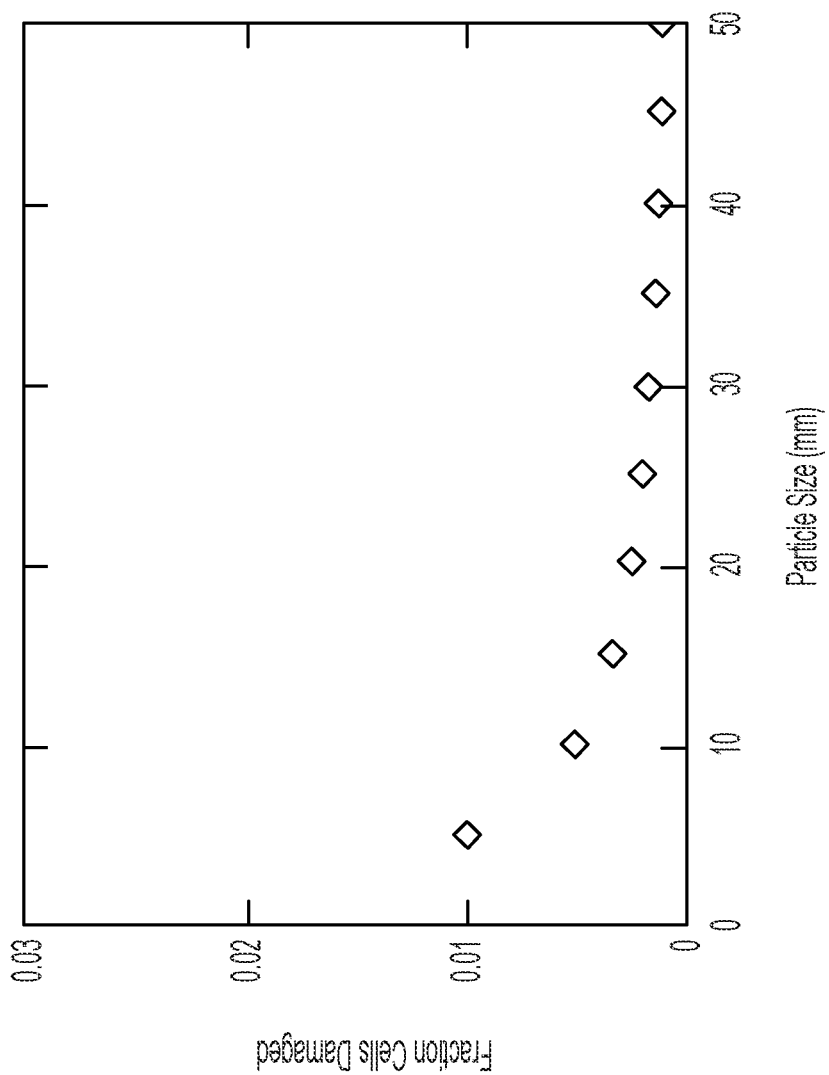
FIG. 2 is a graphical representation of the results of the analysis described in Example 1.

*Cannabis* plant cell damage effectuated by the mechanical breakdown of wet *Cannabis* cuttings was analyzed. The analysis investigated the number of plant cells damaged as a function of the particle size of the discrete wet *Cannabis* particles resulting from mechanical breakdown of *Cannabis* plant leaves and stems. FIG. 2 is a graphical representation of the results of the analysis. As shown in FIG. 2, the fraction of total *Cannabis* plant cells that are damaged and release their contents decreases as the size of the discrete wet *Cannabis* particles increases.

Example 2: Water Released from Breakdown of Wet *Cannabis* Cuttings

Figure 3:
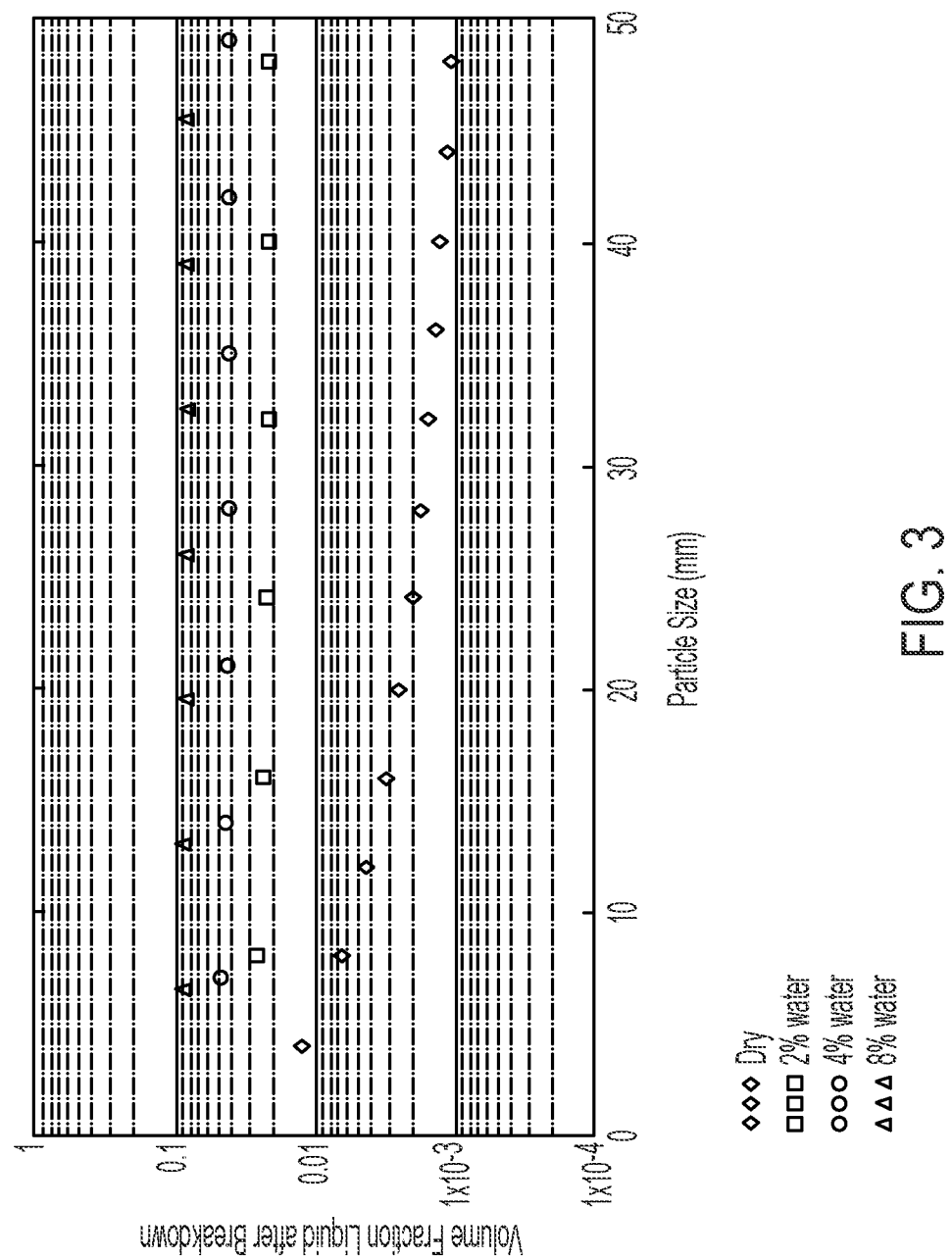
FIG. 3 is a graphical representation of the results of the analysis described in Example 2.

The amount of water released from wet *Cannabis* cuttings as a result of the mechanical breakdown of the wet *Cannabis* cuttings was analyzed. The analysis investigated the volume fraction of liquid (liquid volume/total volume) present after mechanical breakdown of wet *Cannabis* cuttings having different amounts of initial water to discrete wet *Cannabis* particles having different particle sizes. FIG. 3 is a graphical representation of the results of the analysis. As shown in FIG. 3, the volume fraction of liquid decreases as wet *Cannabis* particle size increases, but is also dependent upon the initial volume fraction water present in the wet *Cannabis* cuttings. The initial wetness of the wet *Cannabis* cuttings dominates the volume fraction liquid as cutting the wet *Cannabis* cuttings releases very little liquid, as is observed with the 0% water curve in FIG. 3.

Example 3: Ethanol as Cooling Media for Flash Freezing

The use of ethanol as a cooling media for the disruption of cell walls of plant cells of ground, wet *Cannabis* material by way of flash freezing was analyzed. Flash freezing was modeled using an energy balance, a water and ethanol azeotrope cooling media ("solvent"), the heat capacity of the ground, wet *Cannabis* material, and the heat of fusion of water. The solvent was assumed to enter the flash freezing apparatus at −70° C., and to exit the flash freezing apparatus at the freezing temperature of the *Cannabis* plant (a temperature less than or equal to 0° C., depending on the *Cannabis* plant strain).

Figure 4:
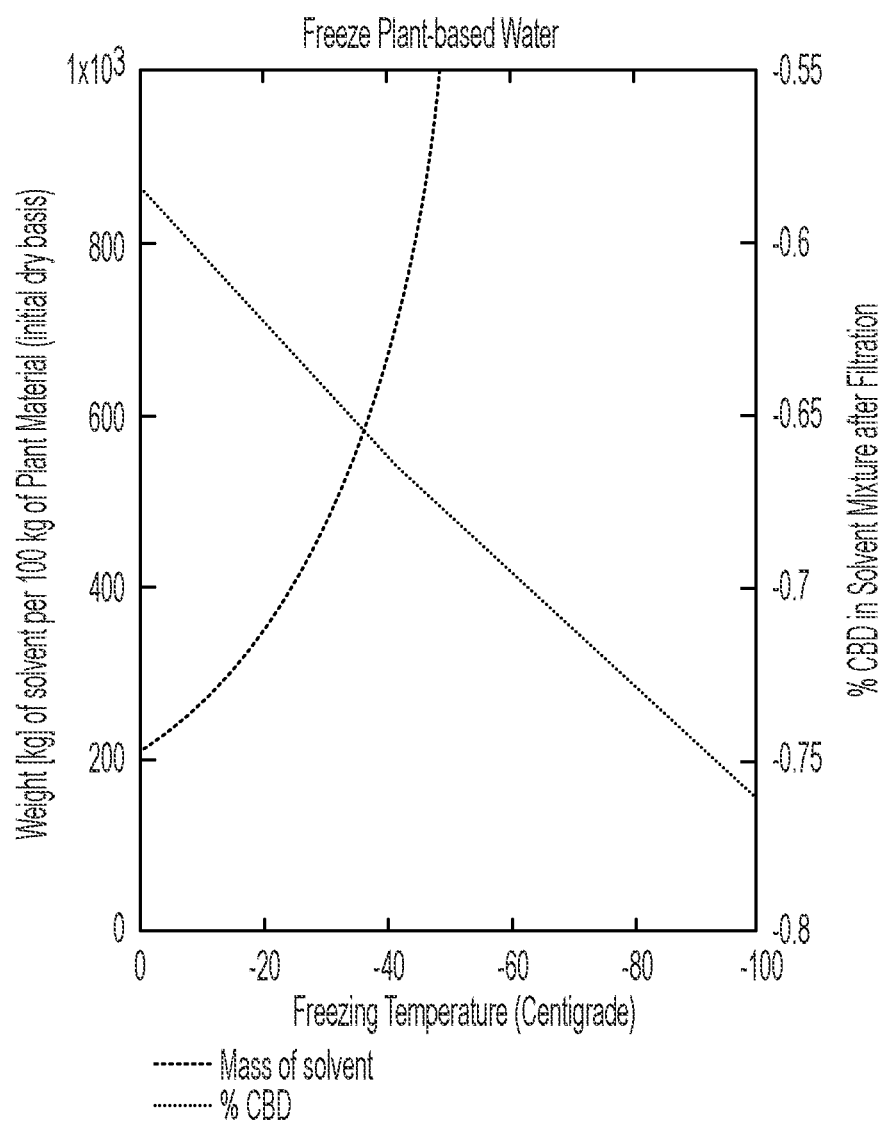
FIGS. 4 and 5 are graphical representations of the results of the analysis described in Example 3.

FIG. 4 is a graphical representation showing the weight of solvent per 100 kilograms (kg) of ground, wet *Cannabis* material (having 10% excess water content) needed to freeze *Cannabis* plant cells of the ground, wet *Cannabis* material as a function of freezing temperature following mixing of the solvent and the ground, wet *Cannabis* material, as well as the estimated fraction (%) of CBD in solvent mixture after filtration of the resulting cellularly-disrupted *Cannabis* effluent. The analysis assumes 1% CBD in the ground, wet *Cannabis* material, and that all of the CBD is present in the solvent mixture after filtration.

Figure 5:
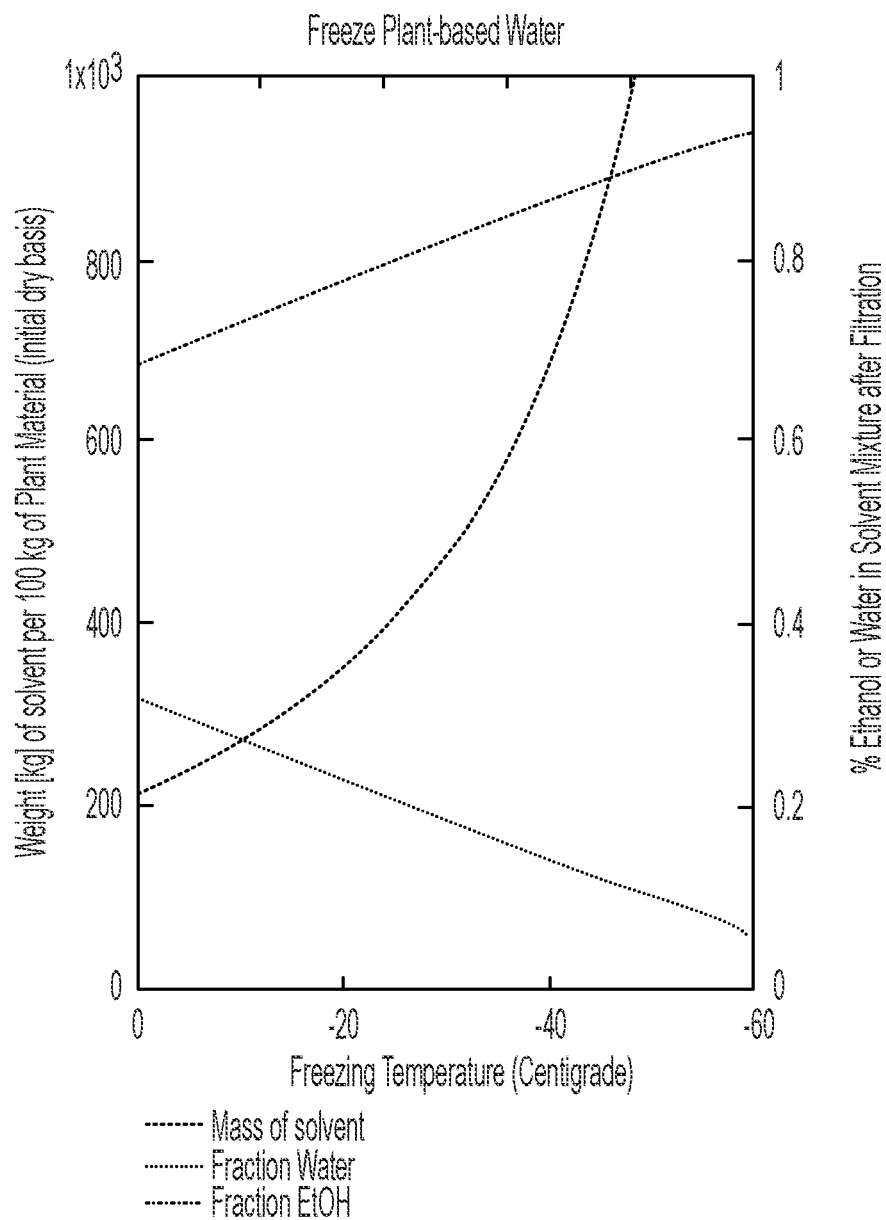

FIG. 5 is a graphical representation showing the weight of ethanol ("solvent") per 100 kg of ground, wet *Cannabis* material (having 10 percent excess water content) needed to freeze *Cannabis* plant cells of the ground, wet *Cannabis* material as a function of flash freezing temperature following mixing of the ethanol and ground, wet *Cannabis* material, as well as the estimated fractions (%) of ethanol and water in solvent mixture after filtration of the resulting cellularly-disrupted *Cannabis* effluent.

Example 4: Cannabinoid Separation

A cannabinoid separation subsystem for use as the at least one separation apparatus 110 (FIG. 1) was modeled and analyzed for conditions wherein the cell disruption apparatus 104 (FIG. 1) comprises a flash freezing apparatus, a cannabinoid extraction solvent is employed as a cooling media for the flash freezing process (in addition to being utilized for cannabinoid extraction following the flash freezing process), and the cannabinoid extraction solvent is recovered and recycled to the flash freezing apparatus following separation of desired cannabinoids therefrom.

Figure 6:
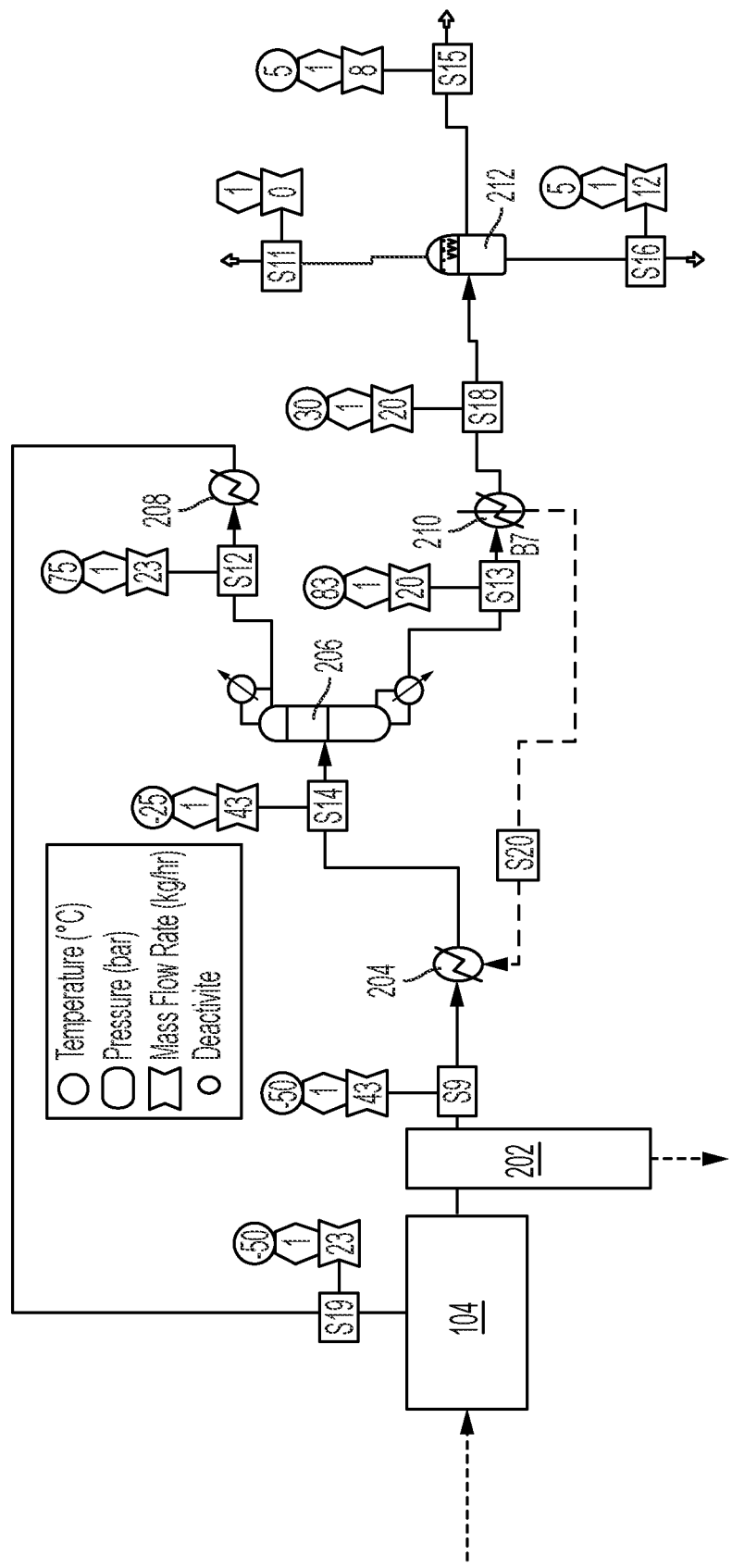
FIG. 6 is a simplified schematic view of a cannabinoid separation subsystem, as described in Example 4.

FIG. 6 is a simplified schematic view of the cannabinoid separation subsystem in use and operation. As shown in FIG. 6, the cannabinoid separation subsystem includes a filter 202, a first heat exchanger 204, a distillation column 206, a second heat exchanger 208, a third heat exchanger 210, and a decanter 212. The filter 202 is downstream of the downstream of the cell disruption apparatus 104 and is figured to separate a solution of the cannabinoid extraction solvent and one or more cannabinoids from other components (e.g., waste) of the cellularly-disrupted *Cannabis* effluent (e.g., the cellularly-disrupted *Cannabis* effluent 120 (FIG. 1)) exiting the cell disruption apparatus 104. The first heat exchanger 204 is downstream of the filter 202, and is configured and operated to receive a first stream S9 from the filter and to produce a second stream S14. The distillation column 206 is downstream of the first heat exchanger 204 and is configured to receive the first stream S9 and produce a third stream S12 and a fourth stream S13. The third stream S12 includes the cannabinoid extraction solvent and is directed to and received by the second heat exchanger 208 to produce a fifth stream S19, which is then recycled back to the cell disruption apparatus 104. The fourth stream S13 includes water and cannabinoids and is directed to and received by the third heat exchanger 210 to produce a sixth stream S18. The sixth stream S18 is directed to and received by the decanter 212 to produce a seventh stream S15 and an eighth stream S16. The seventh stream S15 includes a relatively higher amount (e.g., mass fraction) of water and a relatively lower amount of cannabinoids, and the eighth stream S16 includes a relatively higher amount (e.g., mass fraction) of cannabinoids and a relatively lower amount of water.

FIGS. 7A through 9B are tables showing the properties (e.g., compositions, temperatures, pressures, densities, flowrates) of the streams S9, S12, S13, S14, S15, S16, S18, and S19 of the cannabinoid separation subsystem shown in FIG. 6 using different cannabinoid extraction solvents. FIGS. 7A and 7B show the properties of the streams S9, S12, S13, S14, S15, S16, S18, and S19 using ethanol as the cannabinoid extraction solvent. FIGS. 8A and 8B show the properties of the streams S9, S12, S13, S14, S15, S16, S18, and S19 using isopropanol as the cannabinoid extraction solvent. FIGS. 9A and 9B show the properties of the streams S9, S12, S13, S14, S15, S16, S18, and S19 using n-butanol as the cannabinoid extraction solvent.

While the disclosure is susceptible to various modifications and alternative forms, specific embodiments have been shown by way of example in the drawings and have been described in detail herein. However, the disclosure is not limited to the particular forms disclosed. Rather, the disclosure is to cover all modifications, equivalents, and alternatives falling within the scope of the following appended claims and their legal equivalent. For example, elements and features disclosed in relation to one embodiment may be combined with elements and features disclosed in relation to other embodiments of the disclosure.

What is claimed is:

1. A *cannabis* processing system, comprising:
a cell disruption apparatus configured to disrupt cell walls of plant cells of *cannabis* particles having an average particle size within a range of from about 1 mm to about 3 mm to facilitate removal of one or more cannabinoids within the plant cells of the *cannabis* particles, the cell disruption apparatus comprising one of:
a flash freezing apparatus configured to cool the *cannabis* particles to a temperature within a range of from about −60° C. to about −80° C. in less than or equal to about two (2) minutes and to maintain the temperature for a period of time within a range of from about one (1) minute to about five (5) minutes; and
a spray chamber apparatus configured to form and spray discrete portions of one or more of 4-methylmorpholine 4-oxide (NMMO), an ionic liquid, dimethylsulfoxide (DMSO), paraformaldehyde (PFA), dimethylformamide (DMF), and dimethylacetamide (DMAc) onto to the *cannabis* particles; and
a separation apparatus downstream of the cell disruption apparatus, the separation apparatus configured to separate the one or more cannabinoids from one or more additional chemical compounds of the *cannabis* particles.

2. The *cannabis* processing system of claim 1, further comprising a mechanical disruption apparatus upstream of the cell disruption apparatus and configured to mechanically break down wet *cannabis* cuttings to form a wet *cannabis* material comprising the *cannabis* particles, the mechanical disruption apparatus configured to impart the *cannabis* particles of the wet *cannabis* material with the average an average-particle size within the range of from about 1 mm to about 3 mm.

3. The *cannabis* processing system of claim 2, wherein the mechanical disruption apparatus comprises a grinding apparatus.

4. The *cannabis* processing system of claim 2, further comprising a dewatering apparatus downstream of the mechanical disruption apparatus and upstream of the cell disruption apparatus, the dewatering apparatus configured to mechanically remove from about 75 percent to about 95 percent of intercellular water present within the wet *cannabis* material.

5. The *cannabis* processing system of claim 1, further comprising a wetting apparatus upstream of the cell disruption apparatus, the wetting apparatus configured to wet the *cannabis* particles with one or more solvents before the *cannabis* particles are directed into the cell disruption apparatus.

6. The *cannabis* processing system of claim 1, wherein separation apparatus is configured to separate a solution comprising a cellulose solvent and cellulose from the one or more cannabinoids.

7. A method of processing *cannabis*, comprising:
flash freezing a wet *cannabis* material including *cannabis* particles having an average particle size within a range of from about 1 mm to about 3 mm to disrupt cell walls of plant cells of the *cannabis* particles, the flashing freezing the wet *cannabis* material comprising:
cooling the wet *cannabis* material to a temperature within a range of from about −60° C. to about −80° C. in less than or equal to about two (2) minutes; and
maintaining the wet *cannabis* material at the temperature for a period of time within a range of from about one (1) minute to about five (5) minutes; and
separating one or more cannabinoids of the *cannabis* particles from one or more additional chemical compounds of the *cannabis* particles after flash freezing the *cannabis* particles.

8. The method of claim 7, further comprising mechanically breaking down wet *cannabis* cuttings to form the *cannabis* particles.

9. The method of claim 8, wherein mechanically breaking down the wet *cannabis* cuttings comprises forming the *cannabis* particles to have the average particle size within the range from about 1 mm to about 3 mm.

10. The method of claim 8, further comprising, after mechanically breaking down the wet *cannabis* cuttings and before flash freezing the *cannabis* particles:
pressing *cannabis* material formed by mechanically breaking down the wet *cannabis* cuttings to remove from about 75 percent to about 95 percent of intercellular water from the *cannabis* material and form a partially dewatered *cannabis* material; and
wetting the partially dewatered *cannabis* material with at least one cannabinoid extraction agent to from the wet *cannabis* material including the *cannabis* particles.

11. The method of claim 10, wherein flash freezing the *cannabis* particles comprises:
cooling the wet *cannabis* material to the temperature in less than or equal to about 1 minute; and
maintaining the wet *cannabis* material at the temperature until intracellular fluid of the plant cells of the *cannabis* particles substantially crystallizes.

12. The method of claim 8, wherein separating one or more cannabinoids of the *cannabis* particles from one or more additional chemical compounds of the *cannabis* particles comprises:
combining a cellularly disrupted *cannabis* material formed by flash freezing the wet *cannabis* material including the *cannabis* particles with a cannabinoid extraction solvent to dissolve the one or more cannabinoids and form a cannabinoid solution;
filtering the cellularly disrupted material to separate the cannabinoid solution from other components of the cellularly disrupted material; and
subjecting the cannabinoid solution to one or more of distillation and evaporation to separate the one or more cannabinoids from the cannabinoid extraction solvent.

13. A method of processing *cannabis*, comprising:
treating *cannabis* particles with at least one cellulose solvent to dissolve cell walls of plant cells of the *cannabis* particles, the at least one cellulose solvent selected from 4-methylmorpholine 4-oxide (NMMO), an ionic liquid, dimethylsulfoxide (DMSO), paraformaldehyde (PFA), dimethylformamide (DMF), and dimethylacetamide (DMAc); and
separating one or more cannabinoids of the *cannabis* particles from one or more additional chemical compounds of the *cannabis* particles after treating *cannabis* particles with the at least one cellulose solvent.

14. The method of claim 13, further comprising mechanically breaking down wet *cannabis* cuttings to form the *cannabis* particles, the *cannabis* particles having an average particle size within a range of from about 1 mm to about 3 mm.

15. The method of claim 13, wherein treating *cannabis* particles with at least one cellulose solvent comprises spraying discrete units of the at least one cellulose solvent onto the *cannabis* particles.

16. The method of claim 13, wherein separating one or more cannabinoids of the *cannabis* particles from one or more additional chemical compounds of the *cannabis* particles comprises:
subjecting a cellularly disrupted *cannabis* material formed by treating *cannabis* particles with at least one cellulose solvent to one or more of heat distillation, winterization, and vacuum distillation to separate the cellulose solvent and dissolved cellulose of the cellularly disrupted *cannabis* material from other components of the cellularly disrupted *cannabis* material;
combining the other components of the cellularly disrupted *cannabis* material with a cannabinoid extraction solvent to dissolve the one or more cannabinoids and form a cannabinoid solution; and
subjecting the cannabinoid solution to one or more of distillation and evaporation to separate the one or more cannabinoids from the cannabinoid extraction solvent.

* * * * *

UNITED STATES PATENT AND TRADEMARK OFFICE
CERTIFICATE OF CORRECTION

PATENT NO. : 12,286,415 B2  
APPLICATION NO. : 17/808877  
DATED : April 29, 2025  
INVENTOR(S) : John Moorehead et al.

It is certified that error appears in the above-identified patent and that said Letters Patent is hereby corrected as shown below:

In the Claims

| | | | |
|---|---|---|---|
| Claim 1, | Column 16, | Line 55, | change "from about-60° C." to --from about -60° C.-- |
| Claim 2, | Column 17, | Lines 10-11, | change "the average an average-particle size" to --the average particle size-- |
| Claim 9, | Column 17, | Line 56, | change "range from about" to --range of from about-- |

Signed and Sealed this  
First Day of July, 2025

Coke Morgan Stewart  
*Acting Director of the United States Patent and Trademark Office*